United States Patent
Dupoteau

(10) Patent No.: US 9,792,809 B2
(45) Date of Patent: Oct. 17, 2017

(54) BIO-THREAT ALERT SYSTEM

(75) Inventor: Francois Dupoteau, Toronto (CA)

(73) Assignee: FIO CORPORATION, Toronto (CA)

( * ) Notice: Subject to any disclaimer, the term of this patent is extended or adjusted under 35 U.S.C. 154(b) by 952 days.

(21) Appl. No.: 13/000,953

(22) PCT Filed: Jun. 25, 2009

(86) PCT No.: PCT/CA2009/000882
§ 371 (c)(1),
(2), (4) Date: Mar. 6, 2012

(87) PCT Pub. No.: WO2009/155704
PCT Pub. Date: Dec. 30, 2009

(65) Prior Publication Data
US 2012/0154139 A1 Jun. 21, 2012

Related U.S. Application Data

(60) Provisional application No. 61/075,350, filed on Jun. 25, 2008, provisional application No. 61/093,036, (Continued)

(51) Int. Cl.
*G08B 1/08* (2006.01)
*G08B 27/00* (2006.01)
(Continued)

(52) U.S. Cl.
CPC ....... *G08B 27/005* (2013.01); *G06F 19/3493* (2013.01); *G08B 31/00* (2013.01)

(58) Field of Classification Search
CPC .... G06F 19/3493; G08B 31/00; G08B 27/005
(Continued)

(56) References Cited

U.S. PATENT DOCUMENTS 5,244,630 A 9/1993 Khalil et al.
5,662,824 A 9/1997 Sang et al.
(Continued)

FOREIGN PATENT DOCUMENTS

CA 2061574 8/1992
CA 2021587 4/2003
(Continued)

OTHER PUBLICATIONS

Alivisatos, A.P., Perspectives on the Physical Chemistry of Semiconductor Nanocrystals, Journal of Physical Chemistry, 1996, pp. 13226-13239, vol. 100, No. 31, American Chemical Society, USA.
(Continued)

*Primary Examiner* — Ojiako Nwugo
(74) *Attorney, Agent, or Firm* — DLA Piper LLP (US); Jennifer E. Lacroix

(57) ABSTRACT

In a bio-threat alert infrastructure system and method, an analyzing processor applies statistical algorithms to the collected quantitative data to precisely estimate event data, including time and position data, associated the development of a bio-threat. An encoding processor encodes the event data into a bio-threat alert signal. A transmitting element transmits the signal for reception by a bio-threat alert device. In the bio-threat alert device, and an associated method, a receiving element receives the signal. A decoding processor decodes the signal into the event data. A presentation element presents the event data to a user of the device.

18 Claims, 7 Drawing Sheets

Related U.S. Application Data filed on Aug. 29, 2008, provisional application No. 61/144,283, filed on Jan. 13, 2009.

(51) Int. Cl.
   *G06F 19/00* (2011.01)
   *G08B 31/00* (2006.01)

(58) Field of Classification Search
   USPC .................................................. 340/506
   See application file for complete search history.

(56) References Cited

U.S. PATENT DOCUMENTS

| | | | |
|---|---|---|---|
| 5,714,390 A | 2/1998 | Hallowitz et al. |
| 5,786,219 A | 7/1998 | Zhang et al. |
| 5,817,458 A | 10/1998 | King et al. |
| 5,837,442 A | 11/1998 | Tsang |
| 6,011,252 A | 1/2000 | Jensen |
| 6,022,500 A | 2/2000 | John et al. |
| 6,066,243 A | 5/2000 | Anderson et al. |
| 6,100,541 A | 8/2000 | Nagle et al. |
| 6,103,379 A | 8/2000 | Margel et al. |
| 6,114,038 A | 9/2000 | Castro et al. |
| 6,119,953 A | 9/2000 | Ganan-Calvo et al. |
| 6,172,193 B1 | 1/2001 | Primi et al. |
| 6,174,469 B1 | 1/2001 | Ganan-Calvo |
| 6,261,779 B1 | 7/2001 | Barbera-Guillem et al. |
| 6,274,323 B1 | 8/2001 | Bruchez et al. |
| 6,309,701 B1 | 10/2001 | Barbera-Guillem |
| 6,316,781 B1 | 11/2001 | Nagle et al. |
| 6,319,607 B1 | 11/2001 | Barbera-Guillem et al. |
| 6,333,110 B1 | 12/2001 | Barbera-Guillem |
| 6,340,588 B1 | 1/2002 | Nova et al. |
| 6,353,475 B1 | 3/2002 | Jensen et al. |
| 6,357,670 B2 | 3/2002 | Ganan-Calvo |
| 6,399,952 B1 | 6/2002 | Maher et al. |
| 6,409,900 B1 | 6/2002 | Parce et al. |
| 6,413,401 B1 | 7/2002 | Chow et al. |
| 6,430,512 B1 | 8/2002 | Gallagher |
| 6,468,808 B1 | 10/2002 | Nie et al. |
| 6,494,830 B1 | 12/2002 | Wessel |
| 6,498,353 B2 | 12/2002 | Nagle et al. |
| 6,504,607 B2 | 1/2003 | Jensen et al. |
| 6,506,609 B1 | 1/2003 | Wada et al. |
| 6,514,399 B1 | 2/2003 | Parce et al. |
| 6,524,793 B1 | 2/2003 | Chandler et al. |
| 6,528,165 B2 | 3/2003 | Chandler |
| 6,544,732 B1 | 4/2003 | Chee et al. |
| 6,548,171 B1 | 4/2003 | Barbera-Guillem et al. |
| 6,548,264 B1 | 4/2003 | Tan et al. |
| 6,554,202 B2 | 4/2003 | Ganan-Calvo |
| 6,576,155 B1 | 6/2003 | Barbera-Guillem |
| 6,592,821 B1 | 7/2003 | Wada et al. |
| 6,592,822 B1 | 7/2003 | Chandler |
| 6,630,307 B2 | 10/2003 | Bruchez et al. |
| 6,632,655 B1 | 10/2003 | Mehta et al. |
| 6,649,138 B2 | 11/2003 | Adams et al. |
| 6,673,662 B2 | 1/2004 | Singh |
| 6,680,211 B2 | 1/2004 | Barbera-Guillem et al. |
| 6,699,723 B1 | 3/2004 | Weiss et al. |
| 6,720,411 B2 | 4/2004 | Mirkin et al. |
| 6,734,420 B2 | 5/2004 | Empedocles et al. |
| 6,740,491 B2 | 5/2004 | Mirkin et al. |
| 6,752,966 B1 | 6/2004 | Chazan |
| 6,759,235 B2 | 7/2004 | Empedocles et al. |
| 6,767,706 B2 | 7/2004 | Quake et al. |
| 6,772,070 B2 | 8/2004 | Gilmanshin et al. |
| 6,773,812 B2 | 8/2004 | Chandler et al. |
| 6,778,724 B2 | 8/2004 | Wang et al. |
| 6,787,088 B2 | 9/2004 | Parce et al. |
| 6,835,326 B2 | 12/2004 | Barbera-Guillem |
| 6,864,826 B1 | 3/2005 | Stove |
| 6,872,249 B2 | 3/2005 | Peng et al. |
| 6,881,537 B1 | 4/2005 | Goudsmit et al. |
| 6,881,821 B2 | 4/2005 | Simmonds et al. |
| 6,890,764 B2 | 5/2005 | Chee et al. |
| 6,905,885 B2 | 6/2005 | Colsten et al. |
| 6,966,880 B2 | 11/2005 | Boecker et al. |
| 6,978,212 B1 | 12/2005 | Sunshine |
| 6,986,837 B2 | 1/2006 | Chow et al. |
| 7,024,370 B2 | 4/2006 | Epler et al. |
| 7,037,729 B2 | 5/2006 | Nie et al. |
| 7,041,362 B2 | 5/2006 | Barbera-Guillem |
| 7,069,191 B1 | 6/2006 | Moore |
| 7,077,328 B2 | 7/2006 | Kirchnaswamy et al. |
| 7,079,241 B2 | 7/2006 | Empedocles et al. |
| 7,166,475 B2 | 1/2007 | Colyer et al. |
| 7,171,983 B2 | 2/2007 | Chien et al. |
| 7,192,785 B2 | 3/2007 | Nie et al. |
| 7,243,670 B2 | 7/2007 | Witt et al. |
| 7,252,928 B1 | 8/2007 | Hafeman et al. |
| 7,267,799 B1 | 9/2007 | Borich et al. |
| 7,457,731 B2 | 11/2008 | Rao |
| 8,219,110 B1 * | 7/2012 | White et al. ............... 455/456.1 |
| 2001/0027918 A1 | 10/2001 | Parce et al. |
| 2001/0028055 A1 | 10/2001 | Fafard et al. |
| 2001/0046602 A1 | 11/2001 | Chandler et al. |
| 2001/0055764 A1 | 12/2001 | Empedocles et al. |
| 2002/0009728 A1 | 1/2002 | Bittner et al. |
| 2002/0022273 A1 | 2/2002 | Empedocles et al. |
| 2002/0031783 A1 | 3/2002 | Empedocles et al. |
| 2002/0037499 A1 | 3/2002 | Quake et al. |
| 2002/0045045 A1 | 4/2002 | Adams et al. |
| 2002/0048425 A1 | 4/2002 | McBride et al. |
| 2002/0051971 A1 | 5/2002 | Stuelpnagel et al. |
| 2002/0059030 A1 | 5/2002 | Otworth et al. |
| 2002/0066401 A1 | 6/2002 | Peng et al. |
| 2002/0118355 A1 | 8/2002 | Worthington et al. |
| 2002/0144644 A1 | 10/2002 | Zehnder et al. |
| 2002/0164271 A1 | 11/2002 | Ho |
| 2002/0182609 A1 | 12/2002 | Arcot |
| 2003/0003441 A1 | 1/2003 | Colston et al. |
| 2003/0017264 A1 | 1/2003 | Treadway et al. |
| 2003/0026740 A1 | 2/2003 | Staats |
| 2003/0073086 A1 | 4/2003 | Guire et al. |
| 2003/0099940 A1 | 5/2003 | Empedocles et al. |
| 2003/0132538 A1 | 7/2003 | Chandler |
| 2003/0148530 A1 | 8/2003 | Lauks |
| 2003/0148544 A1 | 8/2003 | Nie et al. |
| 2003/0157327 A1 | 8/2003 | Barbera-Guillem et al. |
| 2003/0165951 A1 | 9/2003 | Bruchez, Jr. et al. |
| 2003/0170613 A1 | 9/2003 | Straus et al. |
| 2003/0172343 A1 | 9/2003 | Leymaster et al. |
| 2003/0175773 A1 | 9/2003 | Chee et al. |
| 2003/0176183 A1 | 9/2003 | Drucker et al. |
| 2003/0177038 A1 | 9/2003 | Rao |
| 2003/0177941 A1 | 9/2003 | Barbera-Guillem |
| 2003/0190628 A1 | 10/2003 | Nakao et al. |
| 2003/0194350 A1 | 10/2003 | Stamatelos et al. |
| 2004/0008125 A1 | 1/2004 | Aratow et al. |
| 2004/0009341 A1 | 1/2004 | Naasani |
| 2004/0067485 A1 | 4/2004 | Mayes et al. |
| 2004/0072428 A1 | 4/2004 | Sato et al. |
| 2004/0096363 A1 | 5/2004 | Porter |
| 2004/0101621 A1 | 5/2004 | Adams et al. |
| 2004/0106218 A1 | 6/2004 | Wang et al. |
| 2004/0118684 A1 | 6/2004 | Wainright et al. |
| 2004/0147031 A1 | 7/2004 | Nakao |
| 2004/0176704 A1 | 9/2004 | Stevens et al. |
| 2004/0203170 A1 | 10/2004 | Barbera-Guillem |
| 2004/0204633 A1 | 10/2004 | Rentea et al. |
| 2004/0229261 A1 | 11/2004 | Young |
| 2004/0241424 A1 | 12/2004 | Barbera-Guillem |
| 2004/0241752 A1 | 12/2004 | Anderson et al. |
| 2004/0247861 A1 | 12/2004 | Naasani |
| 2004/0248167 A1 | 12/2004 | Quake et al. |
| 2004/0266022 A1 | 12/2004 | Sundararajan et al. |
| 2004/0267568 A1 | 12/2004 | Chandler et al. |
| 2005/0004346 A1 | 1/2005 | Dziegiel et al. |
| 2005/0009002 A1 | 1/2005 | Chen et al. |
| 2005/0011764 A1 | 1/2005 | Berndt et al. |
| 2005/0014134 A1 | 1/2005 | West et al. |
| 2005/0032047 A1 | 2/2005 | Simmonds et al. |

(56) References Cited

U.S. PATENT DOCUMENTS

| | | |
|---|---|---|
| 2005/0043894 A1 | 2/2005 | Fernandez et al. |
| 2005/0059030 A1 | 3/2005 | Bao et al. |
| 2005/0071199 A1 | 3/2005 | Riff |
| 2005/0106257 A1 | 5/2005 | Albayrak |
| 2005/0112277 A1 | 5/2005 | Banerjee et al. |
| 2005/0120946 A1 | 6/2005 | Hines et al. |
| 2005/0128479 A1 | 6/2005 | Gilbert et al. |
| 2005/0164264 A1 | 7/2005 | Shipwash |
| 2005/0214536 A1 | 9/2005 | Schrier et al. |
| 2005/0221296 A1 | 10/2005 | Simmonds et al. |
| 2005/0227370 A1 | 10/2005 | Ramel et al. |
| 2005/0239118 A1 | 10/2005 | Goudsmit et al. |
| 2006/0008921 A1 | 1/2006 | Daniels et al. |
| 2006/0012784 A1 | 1/2006 | Ulmer |
| 2006/0014040 A1 | 1/2006 | Peng et al. |
| 2006/0019098 A1 | 1/2006 | Chan et al. |
| 2006/0029267 A1 | 2/2006 | Frost et al. |
| 2006/0046330 A1 | 3/2006 | Chen et al. |
| 2006/0063160 A1 | 3/2006 | West et al. |
| 2006/0068203 A1 | 3/2006 | Ying et al. |
| 2006/0078490 A1 | 4/2006 | Shih et al. |
| 2006/0105335 A1 | 5/2006 | Daehne et al. |
| 2006/0152372 A1 | 7/2006 | Stout |
| 2006/0169800 A1 | 8/2006 | Rosell |
| 2006/0173715 A1 | 8/2006 | Wang |
| 2006/0187017 A1* | 8/2006 | Kulesz et al. ............... 340/506 |
| 2006/0194030 A1 | 8/2006 | Barbera-Guillem |
| 2007/0011722 A1 | 1/2007 | Hoffman et al. |
| 2007/0020779 A1 | 1/2007 | Stavis et al. |
| 2007/0031283 A1 | 2/2007 | Davis et al. |
| 2007/0081920 A1 | 4/2007 | Murphy et al. |
| 2008/0278313 A1* | 11/2008 | Theimer et al. ......... 340/539.13 |
| 2009/0076851 A1 | 3/2009 | Rao |
| 2009/0179756 A1 | 7/2009 | Stout |

FOREIGN PATENT DOCUMENTS

| | | |
|---|---|---|
| CA | 2518352 | 3/2005 |
| CN | 2927206 | 7/2007 |
| EP | 1315099 | 5/2003 |
| JP | 2002-271 | 1/2002 |
| JP | 2005-508493 | 3/2005 |
| WO | 99/19000 | 4/1999 |
| WO | 99/36564 | 7/1999 |
| WO | 99/64840 | 12/1999 |
| WO | 99/66318 | 12/1999 |
| WO | 00/13580 | 3/2000 |
| WO | 00/28598 | 5/2000 |
| WO | 00/70080 | 11/2000 |
| WO | 01/20533 | 3/2001 |
| WO | 01/89585 | 11/2001 |
| WO | 01/93754 | 12/2001 |
| WO | 02/04484 | 1/2002 |
| WO | 03/003015 | 1/2003 |
| WO | 2004/008550 | 1/2004 |
| WO | 2004/040319 | 5/2004 |
| WO | 2005/023923 | 3/2005 |
| WO | 2005/031802 | 4/2005 |
| WO | 2005/052996 | 6/2005 |
| WO | 2005/053649 | 6/2005 |
| WO | 2005/061095 | 7/2005 |
| WO | 2006/033732 | 3/2006 |
| WO | 2006/045004 | 4/2006 |
| WO | 2006/072306 | 7/2006 |
| WO | 2006/132953 | 12/2006 |
| WO | 2007/011622 | 1/2007 |
| WO | 2008/089155 | 7/2008 |
| WO | 2008/147382 | 12/2008 |
| WO | 2009/059404 | 5/2009 |

OTHER PUBLICATIONS

Bakalova, Rurniana et al., Quantum dot-conjugated hybridization probes for preliminary screening of siRNA sequences, Journal of the American Chemical Society, Aug. 1, 2005, pp. 11328-11335, vol. 127, No. 32, American Chemical Society, USA.

Boldt, Klaus et al., Comparative Examination of the Stability of Semiconductor Quantum Dots in Various Biochemical Buffers, Journal of Physical Chemistry B, 2006, pp. 1959-1963, vol. 110, No. 5, American Chemical Society, USA.

Branch, Mary Ann et al., A Subspace, Interior, and Conjugate Gradient Method for Large-Scale Bound-Constrained Minimization Problems, SIAM J. Sci. Comput., Aug. 3, 1999, pp. 1-23, vol. 21, No. 1, Society for Industrial and Applied Mathematics.

Bruchez, Marcel Jr. et al., Semiconductor Nanocrystals as Fluorescent Biological Labels, Science, Sep. 25, 1998, pp. 2013-2015, vol. 281, American Association for the Advancement of Science, USA.

Burns, Mark A. et al., An Integrated Nanoliter DNA Analysis Device, Science, Oct. 16, 1998, pp. 484-487, vol. 282, No. 5388, American Association for the Advancement of Science, USA.

Chabinyc, Michael L. et al., An Integrated Fluorescence Detection System in Poly(dimethylsiloxane) for Microfluidic Applications, Analytical Chemistry, Sep. 15, 2001, pp. 4494-4498, vol. 73, No. 18, American Chemical Society, USA.

Chan, Eugene Y. et al., DNA Mapping Using Microfluidic Stretching and Single-Molecule Detection of Fluorescent Site-Specific Tags, Genome Research, 2004, pp. 1137-1146, vol. 14, Cold Spring Harbour Laboratory Press, USA.

Chan, Warren C.W. et al., Luminescent quantum dots for multiplexed biological detection and imaging, Current Opinion in Biotechnology, 2002, pp. 40-46, vol. 13, Elsevier Science Ltd.

Chan, Warren C.W. et al., Quantum Dot Bioconjugates for Ultrasensitive Nonisotopic Detection, Science, Sep. 25, 1998, pp. 2016-2018, vol. 281, American Association for the Advancement of Science, USA.

Chou, Hou-Pu et al., A microfabricated device for sizing and sorting DNA molecules, PNAS—Proceedings of the National Academy of Sciences of the United States of America, Jan. 1999, pp. 11-13, vol. 96, The National Academy of Sciences, USA.

Dabbousi, B.O. et al., (CdSe)ZnS Core-Shell Quantum Dots: Synthesis and Characterization of a Size Series of Highly Luminescent Nanocrystallites, Journal of Physical Chemistry B, 1997, pp. 9463-9475, vol. 101, No. 46, American Chemical Society, USA.

Duffy, D.C. et al., Rapid Prototyping of Microfulidic Systems in Poly(dimethylsiloxane), Analytical Chemistry, Dec. 1, 1998, pp. 4974-4984, vol. 70, No. 23, American Chemical Society, USA.

Eisenstein, Michael, Technology Feature: Protein Arrays—Growing pains, Losing the Label, an Apt Solution? & (Almost) No Assembly Required, Nature, Dec. 14, 2006, pp. 959-962, vol. 444, Nature Publishing Group, USA.

Fournier-Bidoz, Sebastien et al., Facile and Rapid One-Step Mass Preparation of Quantum-Dot Barcodes, Angewandte Chemie International Edition, 2008, pp. 5577-5581, vol. 47, No. 30, Wiley-VCH Verlag GmbH & Co. KGaA, Weinheim.

Fu, Anne Y. et al., A microfabricated fluorescence-activated cell sorter, Nature Biotechnology, Nov. 1999, pp. 1109-1111, vol. 17, Nature America Inc., USA.

Fu, Lung-Ming et al., Multiple injection techniques for microfluidic sample handling, Electrophoresis, 2003, pp. 3026-3032, vol. 24, Wiley-VCH Verlag GmbH & Co. KGaA, Weinheim.

Gao, Xiaohu et al., In vivo cancer targeting and imaging with semiconductor quantum dots, Nature Biotechnology, Jul. 18, 2004, pp. 969-976, vol. 22, No. 8, Nature Publishing Group, USA.

Gao, Xiaohu et al., Quantum Dot-Encoded Mesoporous Beads with High Brightness and Uniformity: Rapid Readout Using Flow Cytometry, Analytical Chemistry, Apr. 15, 2004, pp. 2406-2410, vol. 76, No. 8, American Chemical Society, USA.

Gao, Xiaohu et al., Quantum-dot nanocrystals for ultrasensitive biological labelling and mulitcolor optical encoding, Journal of Biomedical Optics, Oct. 2002, pp. 532-537, vol. 7, No. 4, SPIE.

Gaponik, Nikolai et al., Toward Encoding Combinatorial Libraries: Charge-Driven Microencapsulation of Semiconductor Nanocrystals Luminescing in the Visible and Near IR, Advanced Materials, Jun. 18, 2002, pp. 879-882, vol. 14, No. 12, Wiley-VCH Verlag GmbH, Weinheim.

(56) References Cited

OTHER PUBLICATIONS

Gershon, Diane, Technology Feature: DNA Microarrays—More than than gene expression, It's a Small World, Microassays Move Downstream & on the Hardware Front, Nature, Oct. 20, 2005, pp. 1195-1198, vol. 437, Nature Publishing Group, USA.
Goluch, E.D. et al., A bio-barcode assay for on-chip attomolar-sensitivity protein detection, Lab on a Chip, Aug. 15, 2006, pp. 1293-1299, vol. 6, The Royal Society of Chemistry.
Grumann, M. et al., Parallelization of Chip-Based Fluorescence Immuno-Assays with Quantum-Dot Labelled Beads, The 13th International Conference on Solid-State Sensors, Actuators and Microsystems, Jun. 2005, pp. 1114-1117, IEEE.
Han, Mingyong et al., Quantum-dot-tagged microbeads for multiplexed optical coding of biomolecules, Nature Biotechnology, Jul. 2001, pp. 631-635, vol. 19, Nature Publishing Group, USA.
Hines, Margaret A. et al., Synthesis and Characterization of Strongly Luminescing ZnS-Capped CdSe Nanocrystals, Journal of Physical Chemistry B, 1996, pp. 468-471, vol. 100, No. 2, American Chemical Society, USA.
Kloepfer, Jeremiah A. et al., Photophysical Properties of Biologically Compatible CdSe Quantum Dot Structures, Journal of Physical Chemistry B, 2005, pp. 9996-10003, vol. 109, No. 20, American Chemical Society, USA.
Klostranec, Jesse M. et al., Convergence of Quantum Dot Barcodes with Microfluidics and Signal Processing for Multiplexed High-Throughput Infectious Disease Diagnostics, Nano Letters, Aug. 18, 2007, pp. 2812-2818, vol. 7, No. 9, American Chemical Society, USA.
Klostranec, Jesse M. et al., Quantum Dots in Biological and Biomedical Research: Recent Progress and Present Challenges, Advanced Materials, Aug. 4, 2006, pp. 1953-1964, vol. 18, No. 15, Wiley-VCH Verlag GmbH & Co. KGaA, Weinheim.
Li, Yougen et al., Multiplexed detection of pathogen DNA with DNA-based fluorescence nanobarcodes, Nature Biotechnology, Jul. 2005, pp. 885-889, vol. 23, No. 7, Nature Publishing Group, USA.
Liu, Wen-Tso et al., Microfluidic device as a new platform for immunofluorescent detection of viruses, Lab on a Chip, Oct. 4, 2005, pp. 1327-1330, vol. 5, The Royal Society of Chemistry.
Malamud, D. et al., Point Detection of Pathogens in Oral Samples, Adv Dent Res, Jun. 2005, pp. 12-16, vol. 18.
Marti et al., Design and characterization of two-dye and three-dye binary fluorescent probes for mRNA detection, Tetrahedron, Mar. 21, 2007, pp. 3591-3600, vol. 63, No. 17, Elsevier Science Publishers, Amsterdam, NL.
Mattoussi, H. et al., Luminescent Quantum Dot-Bioconjugates in Immunoassays, FRET, Biosensing, and Imaging Applications, JALA—Journal of the Association for Laboratory Automation, Feb. 2004, pp. 28-32, vol. 9, No. 1, The Association for Laboratory Automation, USA.
Medintz, Igor L. et al., Quantum dot bioconjugates for imaging, labelling and sensing, Nature Materials, Jun. 2005, pp. 435-446, vol. 4, Nature Publishing Group, USA.
Moré, Jorge J. et al., Computing a Trust Region Step, SIAM J. Sci. Stat. Comput., Sep. 1983, pp. 553-572, vol. 4, No. 3, Society for Industrial and Applied Mathematics.
Murray, C.B. et al., Synthesis and Characterization of Nearly Monodisperse CdE (E=S, Se, Te) Semiconductor Nanocrystallites, Journal of the American Chemical Society, 1993, pp. 8706-8715, vol. 115, No. 19, American Chemical Society, USA.
Neogi, A. et al., Enhanced luminescence efficiency from hydrogel microbead encapsulated quantum dots, Materials Research Society Symposium Proceedings, Jan. 1, 2007, pp. 202-207, vol. 959, Materials Research Society, USA.
Peng, Xiaogang et al., Epitaxial Growth of Highly Luminescent CdSe/CdS Core/Shell Nanocrystals with Photostability and Electronic Accessibility, Journal of the American Chemical Society, 1997, pp. 7019-7029, vol. 119, No. 30, American Chemical Society, USA.
Pregibon, Daniel C. et al., Multifunctional Encoded Particles for High-Throughput Biomolecule Analysis, Science, Mar. 9, 2007, pp. 1393-1396, vol. 315, American Association for the Advancement of Science, USA [downloaded on Mar. 9, 2009 from http://www.sciencemag.org].
Sathe, Tushar R. et al., Mesoporous Silica Beads Embedded With Semiconductor Quantum Dots and Iron Oxide Nanocrystals: Dual-Function Microcarriers for Optical Encoding and Magnetic Separation, Analytical Chemistry, Jul. 20, 2006, pp. 5627-5632, vol. 78, No. 16, American Chemical Society, USA.
Service, Robert F., DNA Analysis: Microchip Arrays Put DNA on the Spot, Science, Oct. 16, 1998, pp. 396-399, vol. 282, No. 5388, American Association for the Advancement of Science, USA [downloaded on Mar. 20, 2008 from http://www.sciencemag.org/cgi/content/full/282/5388/396].
Stavis, Samuel M. et al., Single molecule studies of quantum dot conjugates in a submicrometer fuidic channel, Lab on a Chip, Jan. 13, 2005, pp. 337-343, vol. 5, The Royal Society of Chemistry.
Sukhanova, A. et al., Nanocrystal-encoded fluorescent microbeads for proteomics: Antibody profiling and diagnostics of autoimmune diseases, Nano Letters, Aug. 2007, pp. 2322-2327, vol. 7, No. 8, American Chemical Society, USA.
Thomson, B. et al, Dispersion Copolymerization of Styrene and Divinylbenzee. II. Effect of Crosslinker on Particle Morphology, Journal of Applied Polymer Science, 1996, pp. 2009-2028, vol. 59, John Wiley & Sons, Inc.
Xu, Hongxia et al., Muliplexed SNP genotyping using the Qbead™ system: a quantum dot-encoded microsphere-based assay, Nucleic Acids Research, 2003, pp. 1-10, vol. 31, No. 8, Oxford University Press.
Xuan, Xiangchun et al., Focused electrophoretic motion and selected electrokinetic dispensing of particles of particles and cells in cross-microchannels, Electrophoresis, 2005, pp. 3552-3560, vol. 26, Wiley-VCH Verlag GmbH & co. KGaA, Weinheim.
Yun, Kwang-Seok et al., A microfluidic chip for measurement of biomolecules using a microbead-based quantum dot fluorescence assay, Measurement Science and Technology, 2006, pp. 3178-3183, vol. 17, IOP Publishing Ltd, UK.
Zaytseva, Natalya V. et al., Development of a microfluidic biosensor module for pathogen detection, Lab on a Chip, Jul. 6, 2005, pp. 805-811, vol. 5, The Royal Society of Chemistry.
International Search Report and Written Opinion from PCT/CA2009/000882 dated Oct. 8, 2009.
International Preliminary Report on Patentability from PCT/CA2009/000882 dated Nov. 22, 2010.
English Translation of CN 2927206 published Jul. 25, 2007.

* cited by examiner

BIO-THREAT ALERT SYSTEM

CROSS REFERENCE TO RELATED APPLICATIONS

This application is a U.S. National Stage Application of International Application No. PCT/CA2009/000882 filed Jun. 25, 2009, which claims priority from U.S. Provisional Application No. 61/075,350 filed Jun. 25, 2008, U.S. Provisional Application No. 61/093,036 filed Aug. 29, 2008 and U.S. Provisional Application No. 61/144,283 filed Jan. 13, 2009. The entireties of all the above-listed applications are incorporated herein by reference.

FIELD OF THE INVENTION

The present invention relates generally to awareness and management of bio-threats, and more particularly, to a bio-threat alert infrastructure system and method, a bio-threat alert device, and a method of alerting a user thereof.

BACKGROUND OF THE INVENTION

Existing bio-threat alert devices, systems and methods may have been based on static, or substantially static, information. In the result, the alerts generated by these prior art devices, systems and methods may have been out-of-date, sometimes perhaps dangerously so. Additionally, some prior art bio-threat alert devices, systems and methods may only have afforded excessively slow response times, in comparison to the speed of spread of the virus and/or bio-agent. In the result, the prior art may have been lacking a device, system or method capable of providing timely and accurate alerts concerning active bio-threats.

What may also have been missing from prior art alert devices, systems and methods may have been an ability to provide for the early stage bio-detection of diseases.

Though not essential to the working of the present invention, what may be needed is an alert device, system and/or method (such as that provided according some preferred embodiments of the present invention) which may preferably be integrated inside a diagnostic device. Exemplary diagnostic devices, systems and/or methods may be disclosed in International Patent Application Nos. PCT/CA2007/000211 and PCT/CA2007/002317. Alternately, it may be desirable to integrate an alert device, system and/or method inside a diagnostic device equipped with (a) a data transfer system and/or (b) global positioning and/or localization features. Preferably, in this manner, the alert device, system and method according to the present invention may preferably help to resolve, obviate and/or mitigate one or more of the aforementioned problems and/or shortcomings associated with the prior art.

It may also be advantageous for a diagnostic device—integrating the alert device, system and method according to the present invention—to preferably be able to transfer, in real and/or near real-time, the biological information regarding a bio-agent or bio-threat.

There may be some benefit for such an alert device, system or method to incorporate and/or be associated with a substantially reactive information technology architecture. Together with a diagnostic device, such an alert device, system or method may preferably help to allow precise identification of a potential bio-threat. An alert device, system or method of this type may preferably find advantageous utility, especially insofar as it may provide a substantially useful or complete set of information for stopping or delaying a bio-threat.

Ideally, the alert device, system and method according to the present invention may usefully produce a mapping of the geographic origin of a disease or bio-threat and the parameters of its evolution through a region.

It is an object of one preferred embodiment according to the invention to provide an alert system and/or method.

It is an object of one preferred embodiment according to the invention to provide an alert system and/or method which may preferably identify, or help to identify, a geographic origin of a disease and/or bio-threat.

It is an object of one preferred embodiment according to the invention to provide an alert system and/or method which may preferably identify, or help identify, a geographic origin of a disease and/or bio-threat—preferably based on clinical parameters, sociological data, infrastructure data, and/or geophysics information.

It is an object of one preferred embodiment according to the invention to provide an alert system and/or method which preferably may produce, or help to produce, a mapping of the geographic origin of a disease and/or parameters of its progress and/or evolution through a region.

It is an object of one preferred embodiment according to the invention to provide an alert system and/or method which preferably use a combination of data to produce, or help to produce, a mapping of the geographic origin of a disease and/or parameters of its progress and/or evolution through a region.

It is an object of one preferred embodiment according to the invention to provide an alert system and/or method which may preferably use one or more statistical algorithms and/or probability theory, preferably to identify, or help to identify, the propagation speed, the intensity and/or the most infected area in a very short time, and preferably in real-time (or near real-time).

It is an object of one preferred embodiment according to the invention to provide a system and/or method for use in biological and/or medical applications.

It is an object of the present invention to obviate or mitigate one or more of the aforementioned mentioned disadvantages associated with the prior art, and/or to achieve one or more of the aforementioned objects of the invention.

SUMMARY OF THE INVENTION

According to the invention, there is disclosed a bio-threat alert infrastructure system. The system is for use with a bio-threat alert device and collected quantitative data associated with a bio-threat. The system includes an analyzing processor, an encoding processor, and a transmitting element. The analyzing processor operatively applies one or more statistical algorithms to the collected quantitative data to precisely estimate event data. The event data includes time data and position data associated with an event in the development of a bio-threat. The encoding processor encodes the event data into a bio-threat alert signal. The transmitting element operatively transmits the alert signal for reception by the device.

According to an aspect of one preferred embodiment of the invention, the analyzing processor applies the statistical algorithms with reference to (a) clinical parameters (and/or veterinary and/or public health parameters), (b) sociological data (and/or demographic data), (c) medical infrastructure data, and/or (d) geophysics information.

According to an aspect of one preferred embodiment of the invention, the analyzing processor precisely estimates the event data for at least one said event which (a) occurred at a then previous time at or after a beginning of the bio-threat, (b) is occurring substantially in a then present time, and/or (c) is predicted to occur at a then future time.

According to an aspect of one preferred embodiment of the invention, the analyzing processor precisely estimates the time data of at least one aforesaid event which has occurred, is occurring, and/or is predicted to occur substantially local and/or regional to the device.

According to an aspect of one preferred embodiment of the invention, the analyzing processor precisely estimates the time data and/or the position data of at least one aforesaid event which is personalized to the device based on personal data associated with the device.

According to an aspect of one preferred embodiment of the invention, the analyzing processor precisely estimates the event data in the form of one or more visually presentable (a) textual data, (b) graphical data, and/or (c) colored indicator light data.

According to an aspect of one preferred embodiment of the invention, the analyzing processor precisely estimates the event data in the form of visually and/or audibly presentable data.

According to an aspect of one preferred embodiment of the invention, the analyzing processor precisely estimates the position data of at least one said event in the form of (a) descriptive place name data, (b) numerical co-ordinate system data, and/or (c) graphical map and/or drawing data.

According to an aspect of one preferred embodiment of the invention, the analyzing processor precisely estimates the time data and/or the position data of at least one said event on a local, regional, national, international and/or worldwide scale.

According to an aspect of one preferred embodiment of the invention, the analyzing processor precisely estimates the time data and/or the position data of (a) a progression of the bio-threat towards and/or through a location; (b) a rate of expansion and/or propagation of the bio-threat; (c) an evolution and/or mutation of one or more strains of the bio-threat; (d) an efficacy of one or more bio-markers in identifying the bio-threat; and/or (e) one or more intensities of bio-threat infection and/or a most infected area.

According to an aspect of one preferred embodiment of the invention, the analyzing processor precisely estimates the time data and/or the position data of: an efficacy of one or more treatments for the bio-threat, and/or a resistance of the bio-threat to said one or more treatments.

According to an aspect of one preferred embodiment of the invention, the system also includes a receiving element which operatively receives a result of a bio-threat test from a biological or environmental test reader element of one aforesaid device. The analyzing processor operatively applies the statistical algorithms to the result, along with the collected quantitative data, to precisely estimate the event data.

According to an aspect of one preferred embodiment of the invention, the system is adapted for use with one or more of the following as the device: (a) a biological or environmental test reader device; (b) a disposable, consumable and/or reusable biological or environmental test device; (c) an integrated cell phone and biological or environmental test reader device; (d) a cellular telephone; (e) a mobile communications device; (f) a personal digital assistant; (g) a desktop computer; (h) a laptop computer; (i) a navigation device; (j) a digital audio player; (k) a camera; (l) a gaming device; (m) a television; and (n) a radio.

According to the invention, there is also disclosed a method of transmitting a bio-threat alert signal. The method of transmitting the alert signal is for use with a bio-threat alert infrastructure system and collected quantitative data associated with a bio-threat. The method of transmitting the alert signal includes a statistical analysis step, an encoding step, and a transmitting step. In the statistical analysis step, statistical algorithms are applied to the collected quantitative data, using an analyzing processor of the system, to precisely estimate event data. The event data includes time data and position data associated with an event in the development of a bio-threat. In the encoding step, an encoding processor of the system is used to encode the event data into a bio-threat alert signal. In the transmitting step, the system is used to transmit the bio-threat alert signal.

According to an aspect of one preferred embodiment of the invention, in the statistical analysis step, the analyzing processor applies the statistical algorithms with reference to (a) clinical parameters, (b) sociological data, (c) medical infrastructure data, and/or (d) geophysics information.

According to an aspect of one preferred embodiment of the invention, in the statistical analysis step, the analyzing processor precisely estimates the event data for at least one aforesaid event which (a) occurred at a then previous time at or after a beginning of the bio-threat, (b) is occurring substantially in a then present time, and/or (c) is predicted to occur at a then future time.

According to an aspect of one preferred embodiment of the invention, in the statistical analysis step, the analyzing processor precisely estimates the time data of at least one aforesaid event which has occurred, is occurring, and/or is predicted to occur substantially local and/or regional to the device.

According to an aspect of one preferred embodiment of the invention, in the statistical analysis step, the analyzing processor precisely estimates the time data and/or the position data of at least one aforesaid event which is personalized to the device based on personal data associated with the device.

According to an aspect of one preferred embodiment of the invention, in the statistical analysis step, the analyzing processor precisely estimates the event data in the form of one or more visually presentable (a) textual data, (b) graphical data, and/or (c) colored indicator light data.

According to an aspect of one preferred embodiment of the invention, in the statistical analysis step, the analyzing processor precisely estimates the event data in the form of visually and/or audibly presentable data.

According to an aspect of one preferred embodiment of the invention, in the statistical analysis step, the analyzing processor precisely estimates the position data of at least one aforesaid event in the form of (a) descriptive place name data, (b) numerical co-ordinate system data, and/or (c) graphical map and/or drawing data.

According to an aspect of one preferred embodiment of the invention, in the statistical analysis step, the analyzing processor precisely estimates the time data and/or the position data of at least one aforesaid event on a local, regional, national, international and/or worldwide scale.

According to an aspect of one preferred embodiment of the invention, in the statistical analysis step, the analyzing processor precisely estimates the time data and/or the position data of (a) a progression of the bio-threat towards and/or through a location; (b) a rate of expansion and/or propagation of the bio-threat; (c) an evolution and/or mutation of one or more strains of the bio-threat; (d) an efficacy of one or more bio-markers in identifying the bio-threat; and/or (e) one or more intensities of bio-threat infection and/or a most infected area.

According to an aspect of one preferred embodiment of the invention, in the statistical analysis step, the analyzing processor precisely estimates the time data and/or the position data of: an efficacy of one or more treatments for the bio-threat, and/or a resistance of the bio-threat to said one or more treatments.

According to an aspect of one preferred embodiment of the invention, the method of transmitting the alert signal also includes a receiving step of using the system to receive a result of a bio-threat test. In the statistical analysis step, the analyzing processor operatively applies the statistical algorithms to the result, along with the collected quantitative data, to precisely estimate the event data.

According to an aspect of one preferred embodiment of the invention, in the encoding step, the alert signal is adapted for reception by one or more of the following devices, after the transmitting step: (a) a biological or environmental test reader device; (b) a disposable, consumable and/or reusable biological or environmental test device; (c) an integrated cell phone and biological or environmental test reader device; (d) a cellular telephone; (e) a mobile communications device; (f) a personal digital assistant; (g) a desktop computer; (h) a laptop computer; (i) a navigation device; (j) a digital audio player; (k) a camera; (l) a gaming device; (m) a television; and (n) a radio.

According to the invention, there is also disclosed a bio-threat alert device. The device is for use with a bio-threat alert signal. The device includes a receiving element, a decoding processor, and a presentation element. The receiving element operatively receives the alert signal. The decoding processor decodes the alert signal into event data. The event data includes time data and position data associated with an event in the development of a bio-threat. The presentation element operatively presents at least a portion of the event data to a user of the device.

According to an aspect of one preferred embodiment of the invention, the presentation element operatively presents the time data and/or position data of at least one aforesaid event which (a) occurred at a then previous time at or after a beginning of the bio-threat, (b) is occurring substantially in a then present time, and/or (c) is predicted to occur at a then future time.

According to an aspect of one preferred embodiment of the invention, the device also includes a location element operative to identify a location of the device. The presentation element operatively presents the time data of at least one aforesaid event which has occurred, is occurring, and/or is predicted to occur substantially local and/or regional to the device.

According to an aspect of one preferred embodiment of the invention, the presentation element operatively presents the time data and/or the position data of at least one aforesaid event which is personalized to the device and/or to the user based on personal data associated with the device and/or with the user.

According to an aspect of one preferred embodiment of the invention, the presentation element visually presents the portion of the event data (a) textually, (b) graphically, and/or (c) using one or more colored indicator lights.

According to an aspect of one preferred embodiment of the invention, the presentation element includes (a) a display element to visually present, and/or (b) an audio element for audible presentation of, the portion of the event data to the user.

According to an aspect of one preferred embodiment of the invention, the presentation element operatively presents the position data of at least one aforesaid event (a) descriptively using place names, (b) numerically using a co-ordinate system, and/or (c) graphically using a map and/or drawing.

According to an aspect of one preferred embodiment of the invention, the presentation element operatively presents the time data and/or the position data of at least one aforesaid event on a local, regional, national, international and/or worldwide scale.

According to an aspect of one preferred embodiment of the invention, the presentation element operatively presents the time data and/or the position data of: (a) a progression of the bio-threat towards and/or through a location; (b) a rate of expansion and/or propagation of the bio-threat; (c) an evolution and/or mutation of one or more strains of the bio-threat; (d) an efficacy of one or more bio-markers in identifying the bio-threat; and/or (e) one or more intensities of bio-threat infection and/or a most infected area.

According to an aspect of one preferred embodiment of the invention, the presentation element operatively presents the time data and/or the position data of: an efficacy of one or more treatments for the bio-threat, and/or a resistance of the bio-threat to said one or more treatments.

According to an aspect of one preferred embodiment of the invention, the device also includes: (a) a biological or environmental test reader element operative to test for presence of the bio-threat in a biological or environmental test sample; and (b) a transmitting element to remotely transmit a result of the test.

According to an aspect of one preferred embodiment of the invention, the receiving element, the decoding processor, and the presentation element of the device are together embodied within: (a) a biological or environmental test reader device; (b) a disposable, consumable and/or reusable biological or environmental test device; (c) an integrated cell phone and biological or environmental test reader device; (d) a cellular telephone; (e) a mobile communications device; (f) a personal digital assistant; (g) a desktop computer; (h) a laptop computer; (i) a navigation device; (j) a digital audio player; (k) a camera; (l) a gaming device; (m) a television; and/or (n) a radio.

According to an aspect of one preferred embodiment of the invention, the receiving element is adapted to operatively receive, via a wireless communication network, the alert signal from one or more peer devices.

According to the invention, there is also disclosed a bio-threat alerting method of alerting a user of a bio-threat alert device. The bio-threat alerting method is for use with a bio-threat alert signal. The bio-threat alerting method includes a receiving step, a decoding step and a presentation step. In the receiving step, the device is used to receive the alert signal. In the decoding step, a decoding processor, onboard the device, is used to decode the alert signal into event, data. The event data includes time data and position data associated with an event in the development of a bio-threat. In the presentation step, a presentation element onboard the device is used to present at least a portion of the event data to the user.

According to an aspect of one preferred embodiment of the invention, in the presentation step, the presentation element operatively presents the time data and/or position data of at least one said event which (a) occurred at a then previous time at or after a beginning of the bio-threat, (b) is occurring substantially in a then present time, and/or (c) is predicted to occur at a then future time.

According to an aspect of one preferred embodiment of the invention, the bio-threat alerting method also includes a locating step, before the presentation step, of using the device to identify a location of the device. In the presentation step, the presentation element operatively presents the time data of at least one said event which has occurred, is occurring, and/or is predicted to occur substantially local and/or regional to the device.

According to an aspect of one preferred embodiment of the invention, in the presentation step, the presentation element operatively presents the time data and/or the position data of at least one aforesaid event which is personalized to the device and/or to the user based on personal data associated with the device and/or with the user.

According to an aspect of one preferred embodiment of the invention, in the presentation step, the presentation element visually presents the portion of the event data (a) textually, (b) graphically, and/or (c) using one or more colored indicator lights.

According to an aspect of one preferred embodiment of the invention, in the presentation step, the presentation element visually and/or audibly presents the portion of the event data to the user.

According to an aspect of one preferred embodiment of the invention, in the presentation step, the presentation element operatively presents the position data of at least one aforesaid event (a) descriptively using place names, (b) numerically using a co-ordinate system, and/or (c) graphically using a map and/or drawing.

According to an aspect of one preferred embodiment of the invention, in the presentation step, the presentation element operatively presents the time data and/or the position data of at least one aforesaid event on a local, regional, national, international and/or worldwide scale.

According to an aspect of one preferred embodiment of the invention, in the presentation step, the presentation element operatively presents the time data and/or the position data of: (a) a progression of the bio-threat towards and/or through a location; (b) a rate of expansion and/or propagation of the bio-threat; (c) an evolution and/or mutation of one or more strains of the bio-threat; (d) an efficacy of one or more bio-markers in identifying the bio-threat; and/or (e) one or more intensities of bio-threat infection and/or a most infected area.

According to an aspect of one preferred embodiment of the invention, in the presentation step, the presentation element operatively presents the time data and/or the position data of: an efficacy of one or more treatments for the bio-threat, and/or a resistance of the bio-threat to said one or more treatments.

According to an aspect of one preferred embodiment of the invention, the bio-threat alerting method also includes (a) a biological or environmental test step of using the device to test for presence of the bio-threat in a biological or environmental test sample; and (b) a transmitting step of using the device to remotely transmit a result of said test.

According to an aspect of one preferred embodiment of the invention, the receiving step, the decoding step, and the presentation step are together performed using: (a) a biological or environmental test reader device; (b) a disposable, consumable and/or reusable biological or environmental test device; (c) an integrated cell phone and biological or environmental test reader device; (d) a cellular telephone; (e) a mobile communications device; (f) a personal digital assistant; (g) a desktop computer; (h) a laptop computer; (i) a navigation device; (j) a digital audio player; (k) a camera; (l) a gaming device; (m) a television; and/or (n) a radio.

According to an aspect of one preferred embodiment of the invention, in the receiving step, the device operatively receives, via a wireless communication network, the alert signal from one or more peer devices.

Other advantages, features and characteristics of the present invention, as well as methods of operation and functions of the related elements of the method, system and device, and the combination of steps, parts and economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of the system, device and methods according to the present invention, as to their structure, organization, use, and method of operation, together with further objectives and advantages thereof, will be better understood from the following drawings in which presently preferred embodiments of the invention will now be illustrated by way of example. It is expressly understood, however, that the drawings are for the purpose of illustration and description only, and are not intended as a definition of the limits of the invention. In the accompanying drawings.

DETAILED DESCRIPTION OF THE PREFERRED EMBODIMENTS

Figure 1:
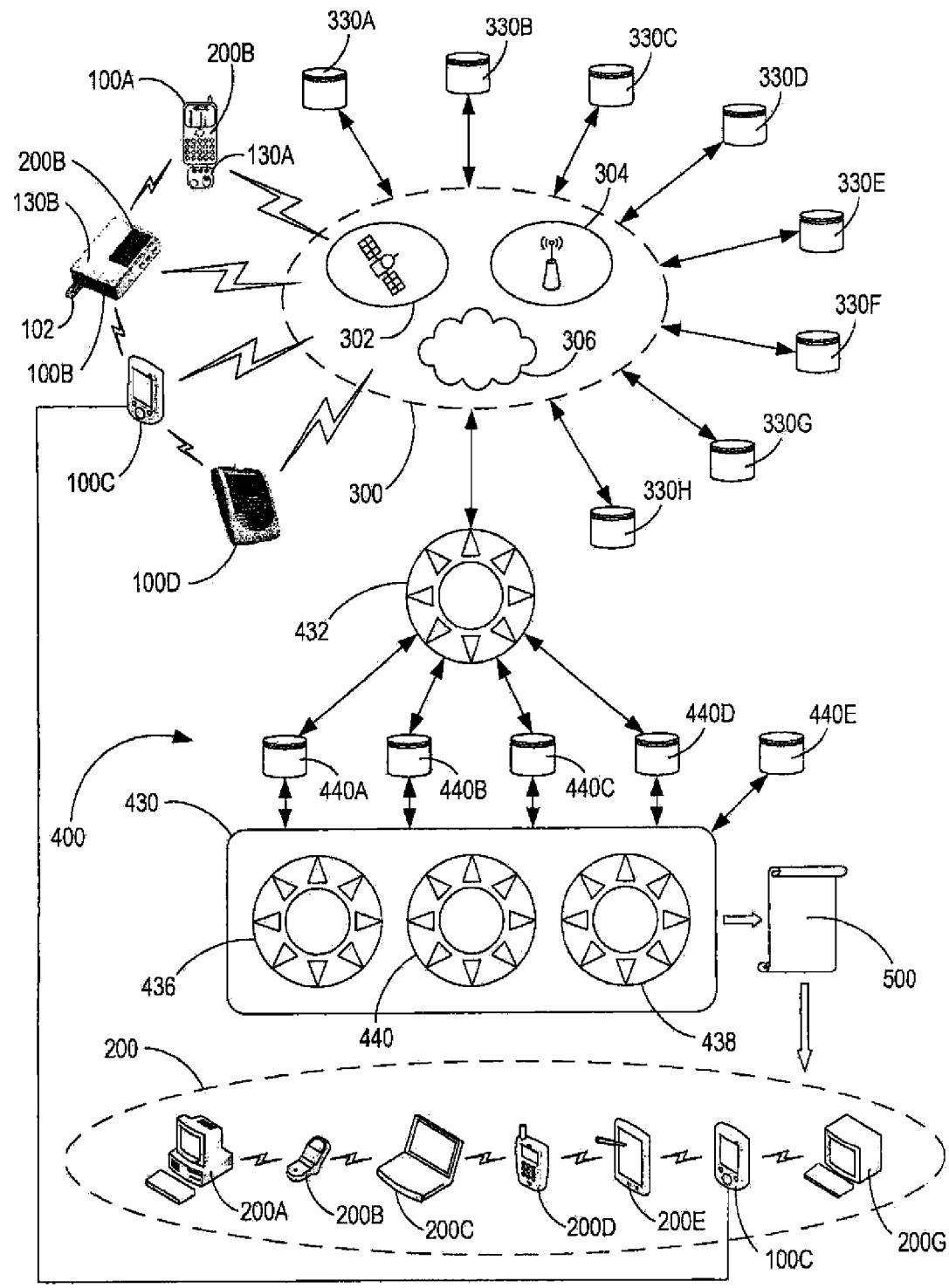
FIG. 1 is a schematic diagram of one bio-threat alert infrastructure system according to the invention.
Figure 2:
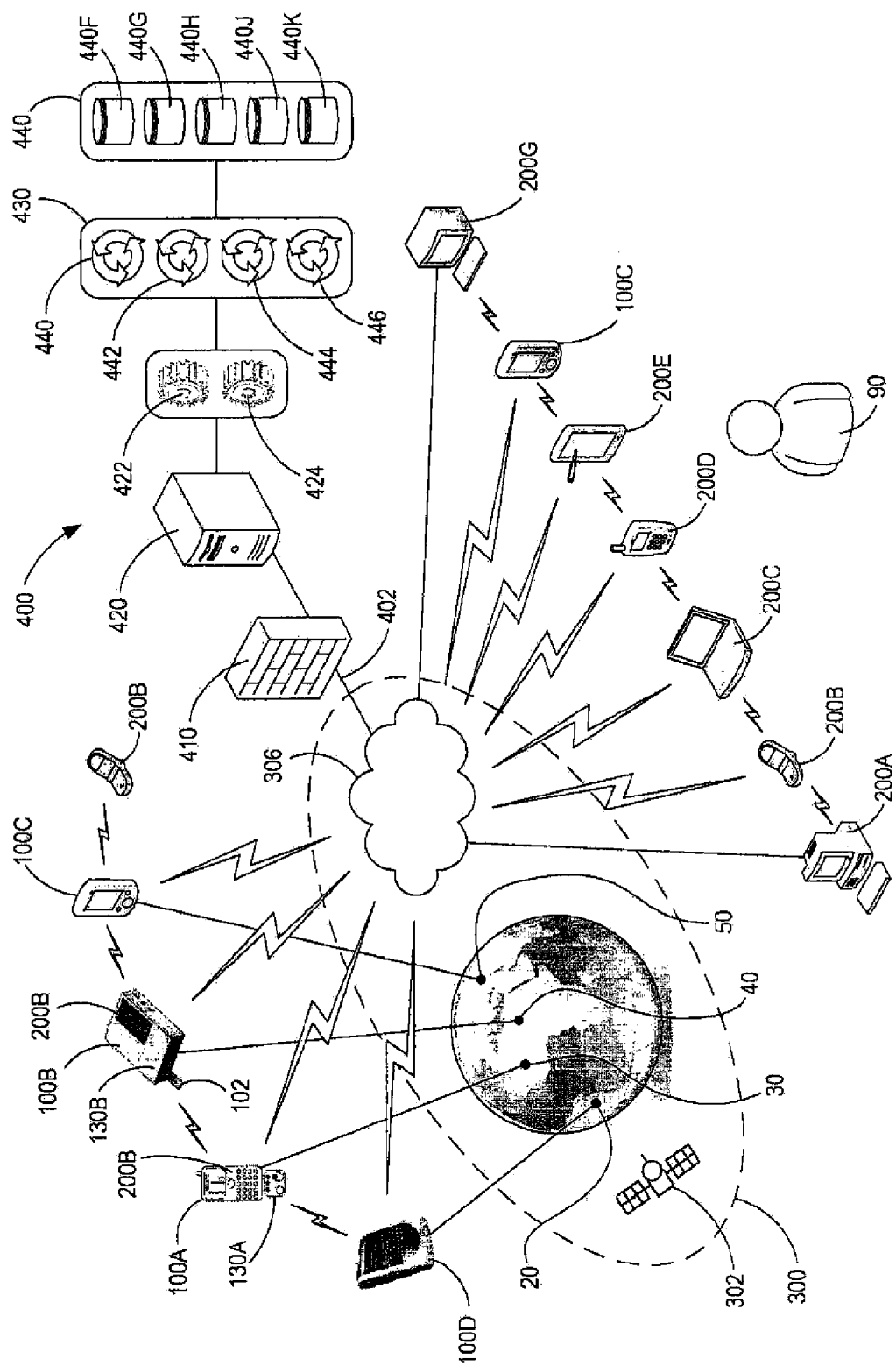
FIG. 2 is a schematic diagram of another bio-threat alert infrastructure system according to the invention.

FIGS. 1 and 2 depict preferred embodiments of a bio-threat alert infrastructure system 400 according to the present invention. In FIGS. 1 and 2, the system 400 is shown in use with communications networks 300. The communications networks 300 may include satellite networks 302 (e.g., GPS networks), a terrestrial wireless network 304 (as shown in FIG. 1), and the Internet 306.

As shown in FIG. 1, various databases may interface with the networks 300, preferably including, without limitation, epidemiologic databases 330A, UN and major/international healthcare institution databases 330B, healthcare and emergency infrastructure databases 330C, education and economic databases 330D, news databases 330E, demographic databases 330F, communication and military infrastructure databases 330G, and weather and topographic databases 330H.

In FIGS. 1 and 2, the system 400 is also shown in use with various bio-threat alert devices, preferably including, without limitation, an integrated cell phone and reusable test device 100A, an integrated cell phone and consumable test device 100B, and dedicated test devices 100C, 100D. FIGS. 1 and 2 also show the system 400 in use with a number of further bio-threat alert devices 200, including, a desktop computer 200A, a cellular telephone 200B, a laptop computer 200C, a mobile communications device 200D (e.g., a smart phone), a personal digital assistant 200E, the dedicated test device 100C, and an Internet terminal 200G. Reference numeral 100 is used to refer to the bio-threat alert devices, collectively. As well, reference numeral 200 is used to refer to alerted ones of the devices. The possible bio-threat alert devices 100 may preferably also include navigation devices, digital audio players, cameras, gaming devices, televisions, and radios, among others. The bio-threat alert devices 100 may preferably be in wireless (and/or wired) communication with one or more of the networks 300.

In FIG. 1, the system 400 is shown to include an interface search application 432 and other software applications 430. The interface search application 432 (alternately, the "interface search engine") is in direct communication with the networks 300 and, indirectly, with the bio-threat alert devices 100 and the aforementioned databases 330A, 330B, 330C, 330D, 330E, 330F, 330G, 330H. The interface search application 432 is, in this sense, both a receiving and a transmitting element. (Among other things, it may receive a result of a bio-threat test from a test reader element 130—alternately, the "test device element"—of the bio-threat alert device 100, as described below.) The interface search application 432 is preferably able to search or "drill-down"—i.e., perform an analytical operation which accesses and/or evaluates detailed data that has been aggregated and/or interrelated—for information inside the aforementioned databases 330A, 330B, 330C, 330D, 330E, 330F, 330G and 330H via the networks 300.

When targeted information is retrieved, according to the invention, the interface search engine 432 preferably dispatches the targeted data into four or more adaptive databases—including a clinical and healthcare database 440A, a sociological database 440B, an infrastructure database 440C, and a geophysics database 440D. The collected data is preferably processed, and/or quantified if necessary, in order to enable and/or facilitate its use by the other software applications 430.

The clinical and healthcare database 440A may preferably contain, among other things, diagnostic and medical data (clinical information), such as, for example, one or more of the following forms of collected quantitative data: (a) test results from diagnostic devices equipped with remote data transfer systems and/or global positioning or localization features; (b) information from UN databases and major healthcare international institutions; and/or (c) scenarios and knowledge data. (The aforesaid scenarios and knowledge data may alternately, or additionally, be provided in a separate scenarios and knowledge database 440E—as discussed below.)

The sociological database 440B may preferably contain, among other things, sociological data (human information), such as, for example, one or more of the following forms of collected quantitative data: (a) population information from local and/or international demographic databases; (b) political and/or organization systems in the area and/or from international databases; (c) education and/or economic systems in the area and/or from international databases; and/or (d) information from news and/or newspapers, drawn from the Internet 306 or elsewhere.

The infrastructure database 440C may preferably contain, among other things, infrastructure data or information, such as, for example, one or more of the following forms of collected quantitative data: (a) information concerning healthcare infrastructure; (b) information concerning communication infrastructures; and/or (c) information concerning emergency and/or military infrastructure; all preferably drawn from local and/or international databases.

The geophysics database 440D may preferably contain, among other things, geophysics data or information, such as, for example, one or more of the following forms of collected quantitative data: (a) weather and/or climatic information from local databases; and/or (b) topographic information from local and/or international databases.

The software applications 430 (alternately, the "core engine" or the "bio-threat alert engine") include a data search application 436, graphical user interface applications 438, and an analysis application 440. The system 400 of FIG. 1 may preferably include one or more processors (not shown) to execute the analysis application 440. Such processors may preferably be similar to an analyzing processor 422 of the embodiment shown in FIG. 2, which is discussed in greater detail below. The bio-threat alert engine 430 is in communication with the clinical and healthcare database 440A, the sociological database 440B, the infrastructure database 440C, and the geophysics database 440D.

The data search application 436 (alternately, the "data search engine") is preferably in charge of searching and/or preparing the data for the analysis application 440.

The analysis application 440 (alternately, the "analysis algorithm") is preferably used to analyze and/or identify a bio-threat and/or disease, with the aid of one or more statistical algorithms which are applied to the collected quantitative data in the adaptive databases 440A, 440B, 440C, 440D (and, in some embodiments, to any collected quantitative data in the scenarios and knowledge database 440E, which is discussed in further detail below).

The graphical user interface applications 438 (alternately, the "GUI algorithm") is preferably used to build a report and/or mapping. The report and/or mapping may preferably be sent and/or presented to healthcare authorities, to emergency staff, and/or to the government.

The data and/or information used according to the present invention may preferably be updated daily, weekly and/or monthly depending on the type of data and/or the level of importance inherent in, and/or assigned to, each type of data. Some of the data may preferably be downloaded from the Internet 306, by satellite networks 302 or a wireless network 304.

As mentioned above, the bio-threat alert engine 430 also preferably may be in communication with an external stand-alone embodiment of the scenarios and knowledge database 440E. The scenarios and knowledge database 440E is preferably used as a repository for at least part, and preferably all, of the information and/or modelization which may be useful in the identification of bio-threats.

With reference to the aforementioned databases 440A, 440B, 440C, 440D and 440E, the bio-threat alert engine 430 of the system 400 may preferably precisely estimate event data associated with an "event" in the development of a bio-threat. The potential events which may be the subject of the event data are not intended to be unduly limited, but may include one or more of the following events, among others: (a) a progression of the bio-threat towards and/or through a location; (b) a static or changing rate of expansion and/or propagation of the bio-threat; (c) an evolution and/or mutation of one or more strains of the bio-threat; (d) an efficacy of one or more bio-markers in identifying the bio-threat; (e) one or more intensities of bio-threat infection and/or a most infected area; and/or (f) an efficacy clone or more treatments for the bio-threat, or a resistance of the bio-threat to the treatments. These and other events may be measured against a local, regional national, international and/or worldwide scale. Also included are events which may be substantially local and/or regional to the device, and/or otherwise personalized to the device and/or its user. Still further, the events may be past events, current events, and/or possible future events. The event data may preferably include, among other things, time data and/or position data associated with the aforesaid event.

The event data is precisely estimated by the system 400, preferably for presentation by the bio-threat alert devices 100, in the form of visually and/or audibly presentable data. Audibly presentable data may take the form of a verbal, musical, tonal and/or other alert sounds. As women, children and men may be thought to have differing sensitivities from each other to some types of sounds, it may be preferable (according to some embodiments of the invention) to adapt the audibly presentable data to be only audible to one or more intended segments of listeners.

Figure 4:
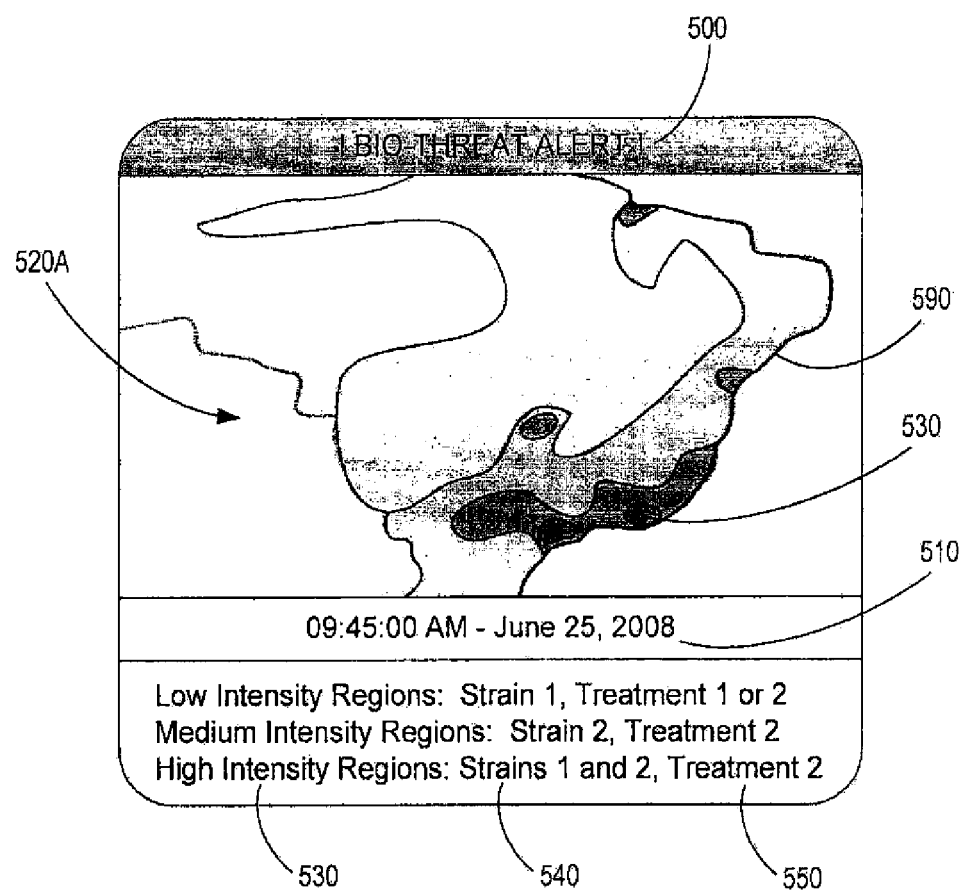
FIG. 4 is graphic representation of one bio-threat alert presented on a display of the bio-threat alert device according to the invention.
Figure 5:
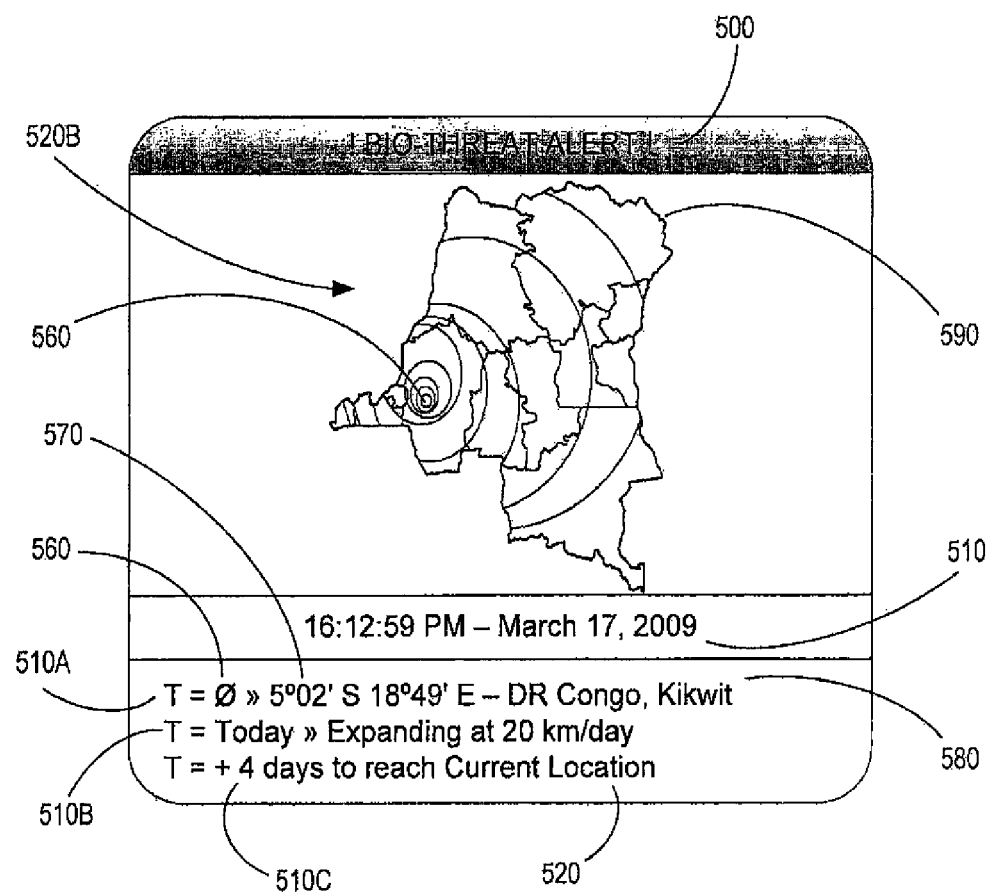
FIG. 5 is graphic representation of another bio-threat alert presented on a display of the bio-threat alert device according to the invention.

Visually presentable data may take the form of text, graphics and/or colored indicator lights. FIGS. 4 and 5, which are discussed in detail below, illustrate some of the different forms of visually presentable data which are contemplated according to the present invention. Among other things, graphical data include maps, drawings, and/or photographs. Map and/or drawing data 590 is illustrated in FIGS. 4 and 5. By way of example, and among other things, visually and/or audibly presentable data may include descriptive and/or numerical data. Exemplary types of descriptive data may include place names, and/or biomarker, bio-threat strain, treatment and/or intensity information. Intensity, strain and treatment data—reference numerals 530, 540 and 550 respectively—is shown in FIG. 4. Exemplary types of numerical data may include numerical co-ordinate system data 570 (e.g., latitude and longitude), as shown in FIG. 5, or data according to other numerical conventions (e.g., conventional measurements of time).

The precision of the estimate performed by the system 400 will, naturally, be affected by the degree of precision present in the underlying collected quantitative data. Nonetheless, the estimated event data is precise at least insofar as the estimate may preferably be substantially reproducible.

The system 400 of FIG. 1 may preferably include one or more further processors (not shown) to encode the event data into a bio-threat alert signal 500, as shown in FIG. 1. Such processors may preferably be similar to an encoding processor 424 of the embodiment shown in FIG. 2, which is discussed in greater detail below.

Preferably, the embodiment of the system 400 which is shown in FIG. 1 may also include a transmitting element (not shown). Such a transmitting element may preferably take a form similar to a network infrastructure connection 402 of the embodiment shown in FIG. 2, which is discussed below. Alternately, any transmitting element of the system 400, as shown in FIG. 1, may be in wired at wireless communication, as appropriate, with any one of the networks 300. In any case, after the system 400 generates the bio-threat alert signal 500, it is transmitted from the system 400 to alerted ones of the aforesaid devices 200. It is noted that one of the alerted ones of the aforesaid devices 200—namely, the dedicated test device 100—may supply geographic location and/or personal data with the system 400 via the networks 300. In FIG. 1, the two instances of the dedicated test device 100C are, therefore, shown joined by a line of communication (since they may very well be one and the same device). It is perhaps worthwhile to also mention that, in FIG. 1, the transmission of the alert signal 500 to the alerted ones of the aforesaid devices 200 may preferably be made via one or more of the networks 300.

With reference to the embodiment of the system 400 which is shown in FIG. 1, the device 100 and associated methods 600, 700 which are discussed above, it will be appreciated by one skilled in the art that, although some of the components, relations, processes and aspects thereof are not specifically referenced in the following discussion of same and of the embodiment of the system 400 which is shown in FIG. 2, they may be used, and/or adapted for use, in association therewith.

Now, with specific reference to FIG. 2, there is shown another preferred embodiment of the system 400. The system 400 is preferably, behind a firewall 410, in communication with the Internet 306 by the aforesaid network infrastructure connection 402.

FIG. 2 again shows the system 400 in use with communications networks 300, preferably including satellite networks 302 (e.g., GPS networks) and the Internet 306, among others. The devices 100A, 100B, 100C and 100D are shown at geographic locations 30, 40, 50 and 20, respectively. The desktop computer 200A and the Internet terminal 200G are shown in wired connection with the Internet 306. In FIG. 2, the cellular telephone 200B, the laptop computer 200C, the mobile communications device 200D, the personal digital assistant 200E, and the dedicated test device 100C are shown in wireless communication with the networks 300. A user 90 may operate one or more of the devices 200A, 200B, 200C, 200D, 200E, 1000, 200G.

In FIG. 2, the system 400 is shown to include an alert data broker 420, as the front-end for the aforesaid analyzing processor 422 and the aforesaid encoding processor 424. The data broker 420 may preferably disseminate and/or provide, among other things, one or more of the following: service and support for treatments; education (e.g., CME); advertisements (e.g., advertising new drugs to doctors); medication information on-board; information concerning the geographic location of the devices 100; subscription community management; statistics on spatial and temporal identification (ID) data; information concerning origin and rate of expansion in case of a pandemic onset; information concerning the efficacy of a particular biomarker which may be used; a collection of observations and/or opinions from doctors; alert reports for cellular phones; and/or an online portal for IDs.

The processors 422, 424 work in conjunction with the software applications 430. The software applications 430 shown in FIG. 2 include the analysis application 440, services applications 442, data management applications 444, and diagnostic panel applications 446. In FIG. 2, the software applications 430 are shown in communication with the following adaptive databases 440: a clinical tests database 440F, an identification (ID) panels database 440G, a quality control database 440H, a service database 4403, and a surveillance database 440K.

The service database 440J may preferably disseminate and/or provide, among other things, one or more of the following: service and support for test administration; service and support for treatments; education (e.g., CME); advertisements (e.g., advertising new drugs to doctors); medication information on-board; information concerning the geographic location of the devices 100; information concerning the number of tests administered per device 100; subscription community management; usage monitoring; inventory tracking; information concerning the quality control database 440H; and/or an ability to track errors by the user 90.

The surveillance database 440K may preferably disseminate and/or provide, among other things, one or more of the following: statistics on spatial and temporal identification (ID) data; information concerning origin and rate of expansion in case of a pandemic onset; information concerning the efficacy of a particular biomarker which may be used; information concerning representative levels of particular biomarkers per region; a collection of observations and/or opinions from doctors; peer ratings on the information collected; profile information concerning buyers and/or vendors to create profiled content and/or to increase transactions; alert reports for cellular phones; and/or an online portal for IDs.

Figure 3:
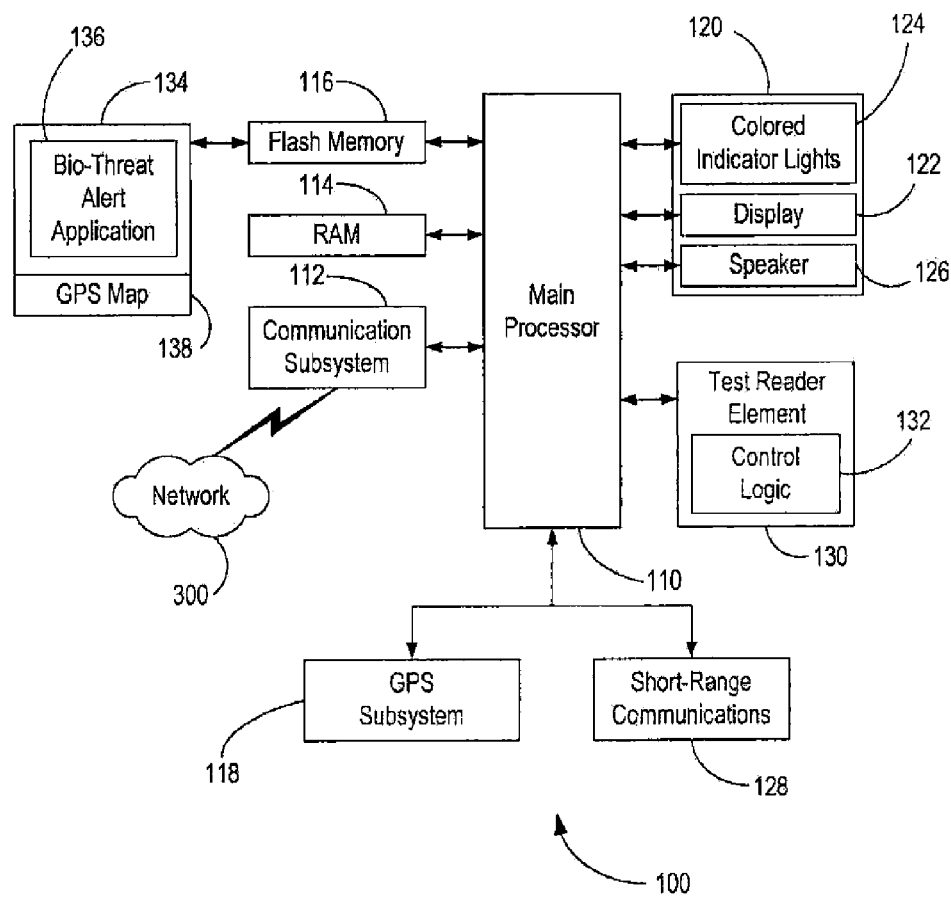
FIG. 3 is a schematic block diagram of components of a bio-threat alert device according to the invention.

Preferably, as shown in FIG. 3, some of the bio-threat alert devices 100 may include the aforesaid test device element 130 working in conjunction with a main processor 110. In an illustrative embodiment, the invention may be practiced with one of the aforesaid devices 100 in a wireless operating environment. Shown in FIG. 3 is a schematic block diagram of an illustrative one of the bio-threat alert devices 100. The bio-threat alert device 100 may include a number of components, including the aforementioned main processor 110 which may preferably control the overall operation of the device 100. Communication functions, including data and voice communications, may be performed through a communication subsystem 112. The communication subsystem 112 preferably acts as both a receiving element and a transmitting element. The communication subsystem 112 may receive messages from and send messages to a wireless network 300. The device 100 may send and receive communication signals over the networks 300.

Some of the subsystems of the bio-threat alert device 100 may perform communication-related functions, and some may provide "resident" or on-device functions. By way of example, a display 122 may be used for both functions.

The main processor 110 may also interact with additional subsystems, such as a random access memory (RAM) 114, a flash memory 116, a presentation element 120 (preferably including, for example, the display 122, colored indicator lights 124, and a speaker 126), short-range communications 128, a GPS subsystem 118, and the test device element 130. Still referring to FIG. 3, operating system software used by the main processor 110 is typically stored in a persistent store such as the flash memory 116. Those skilled in the art will appreciate that the operating system, specific device applications, or parts thereof, may be temporarily loaded into a volatile store, such as the RAM 114, for processing by main processor 110.

The GPS subsystem 118 may be operatively connected to the main processor 110 to pass acquired latitude and longitude coordinates to one or more software applications 134, and to store the latitude and longitude coordinates as may be required into flash memory 116 or RAM 114. The main processor 110, in addition to its operating system functions, enables execution of various software applications 134 on the device 100. The software applications 134 may include a GPS map application 138 for providing geographic navigation, and location coordinates for geo-tagging objects. The GPS map application 138 may be configured to operatively connect to the GPS subsystem 118 to receive GPS latitude and longitude coordinates for a current position of the device 100. The GPS map application 138 may also store scalable maps of various geographic regions in order to show the current position of the device 100 on the map. As well, the GPS map application 138 may be configured to obtain latitude and longitude location coordinates by allowing a user to select a position on the UPS map.

As described elsewhere herein, in order to transmit test data to the system 400, the test device element 130 may be provided with control logic 132. As aforesaid, the test device element 130 may be operatively connected to the main processor 110. As such, the test device element 130 may pass acquired test data to one or more software applications 134, to the communication subsystem 112, and to store the test data as may be required into flash memory 116 or RAM 114. The test device element 130 may be directly initiated by the user 90. Additionally, the bio-threat alert application 136 may be directly and/or indirectly initiated by the user 90—in addition to by the bio-threat alert signal 500 received from the bio-threat alert infrastructure system 400—by controlling a dedicated alert button or a context dependent programmable button or key that may double as a bio-threat alert button.

Preferably, when the bio-threat alert signal 500 is received by the communication subsystem 112 of the device 100, the main processor 110 launches the bio-threat alert application 136. Together, the bio-threat alert application 136 and the main processor 110 decode the signal 500 into the event data. The event data is then presented to the user 90 using the display 122, the colored indicator lights 124, and/or the speaker 126 of the presentation element 120, as appropriate.

FIGS. 4 and 5 graphically depict decoded bio-threat alert signals 500 which may preferably be presented on the displays 122 of the alert devices 100 according to the present invention. In FIG. 4, time data 510 is shown in a textual format, and regional position data 520A is shown graphically in the form of map and/or drawing data 590. Intensity data 530 is shown both in textual and graphical formats. FIG. 4 also includes strain mutation data 540 and treatment efficacy data 550 in textual format.

FIG. 5 shows time and position data 510 and 520 respectively, in a textual format, and graphically displays national position data 520B. In FIG. 5, the time data 510 includes past, present and future time data, 510A, 510B and 510C respectively. Point of origin data 560 is shown in textual and graphical formats, the latter as map and/or drawing data 590. FIG. 5 shows numerical co-ordinate system data 570 and textual/descriptive place name data 580.

It is noted that FIG. 5 includes an estimate of the number of days remaining before a particular bio-threat reaches the current location 520 of the device 100. It will be appreciated, therefore, that it is necessary for the device 100 to provide its geographic location 20, 30, 40 or 50 to the system 400. In FIG. 1, for example, one of the alerted ones of the devices 200—namely, the dedicated test device 100C—may supply its geographic location and/or personal data with the system 400 via the networks 300. In this last respect, it may be worthwhile to mention that, just as the bio-threat alert signal 500 may be customized to the device 100 on the basis of its location, the signal 500 may be customized on the basis of personal data associated with the user 90 and/or the device 100. That is, for example, the signal 500 may be customized on the basis of the health or bio-threat predisposition of the user 90.

Figure 6:
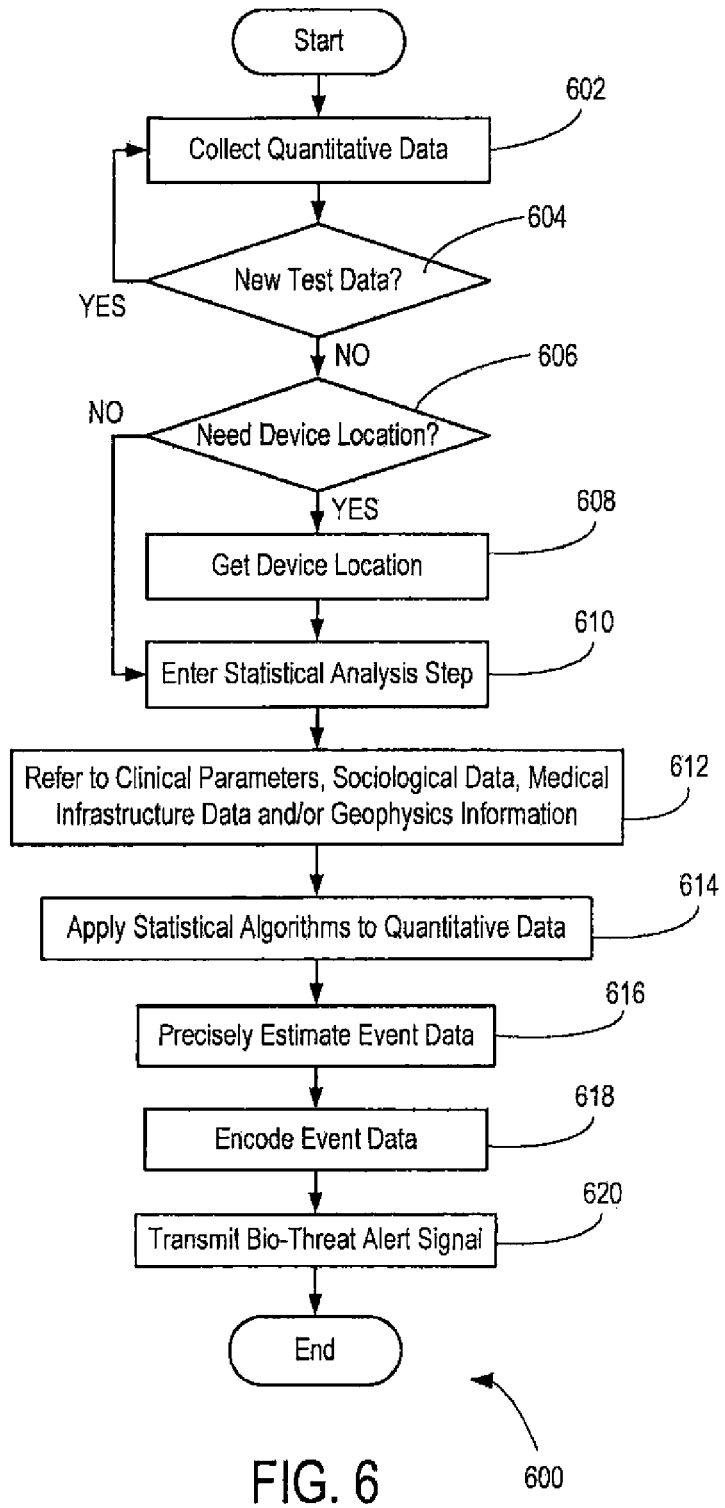
FIG. 6 is a flowchart of an illustrative method of transmitting a bio-threat alert signal according to the invention.

FIG. 6 shows, schematically by way of overview, an associated method 600 of transmitting the bio-threat alert signal 500. The method includes the following steps, among others: a data collection step 602, a test step 604, a location query 606, a device locating step 608, a statistical analysis step 610, an encoding step 618, and a transmitting step 620.

In the data collection step 602—alternately, the "receiving step"—the method 600 uses the system 400 to receive (among other things) a result of a bio-threat test conducting during or after the test step 604.

For the transmission of some types of event data, the system 400 requires the geographic location 20, 30 40, 50 of the device 100. In such event, the method 600 answers the location query 606 in the affirmative. In the device locating step 608, the method 600 then obtains the location 20, 30, 40, 50 for the device 100.

The statistical analysis step includes a reference substep 612, an apply algorithms substep 614, and a generate event data substep 616. In the reference substep 612 of the statistical analysis step 610, the analyzing processor 422 applies the statistical algorithms with reference to (a) clinical parameters, (b) sociological data, (c) medical infrastructure data, and/or (d) geophysics information. In the apply algorithms substep 614 of the statistical analysis step 610, the statistical algorithms are applied to the collected quantitative data, using the analyzing processor 422 of the system 400. After applying the algorithms, the system 400 then precisely estimates the event data in the generate event data substep 616 of the statistical analysis step 610.

In the encoding step 618, the encoding processor 424 of the system 400 is used to encode the event data into the bio-threat alert signal 500. In the transmitting step, the system 400 is used to transmit the bio-threat alert signal 500.

Figure 7:
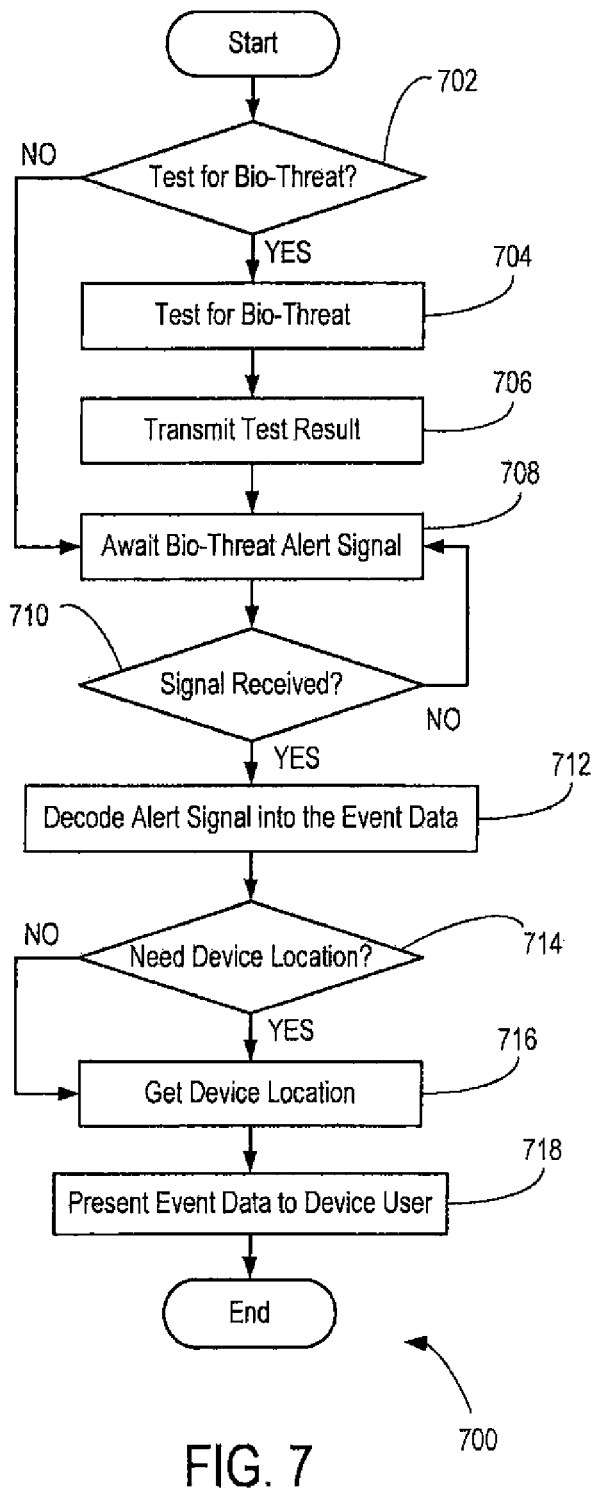
FIG. 7 is a flowchart of an illustrative method of alerting a user of a bio-threat alert device according to the invention.

FIG. 7 shows, schematically by way of overview, an associated bio-threat alerting method 700. The method includes the following steps, among others: a test query 702, a test step 704, a transmitting step 706, an await alert step 708, a receiving step 710, a decoding step 712, a location query 714, a device locating step 716, and a presentation step 718.

If a test is to be conducted for a bio-threat, the method 700 answers the test query 702 in the affirmative. In the test step 704, the test reader element 130 of the device 100 is used to test for presence of the bio-threat in a biological or environmental test sample. Thereafter, in the transmitting step 706, the communication subsystem 112 of the device 100 is used to remotely transmit a result of the test.

Thereafter, in the await alert step 708, the method 700 awaits reception of the bio-threat alert signal 500. In the receiving step 710, the communication subsystem 112 of the device 100 is used to receive the alert signal 500. In the receiving step 710, the device 100 receive the alert signal 500, via the networks 300, from the system 400 and/or from another one or more of the devices 100 (i.e., from peer devices), as shown in FIGS. 1 and 2.

In the decoding step 712, a decoding processor (preferably, a dedicated or tasked activity of the main processor 110 onboard the device 100) is used to decode the alert signal 500 into the event data.

To obtain some types of event data, the device 100 needs to provide its geographic location 20, 30 40 or 50. In such event, the method 700 answers the location query 714 in the affirmative. In the locating step 716, the device 100 is used to identify its own location 20, 30, 40 or 50.

In the presentation step 718, the presentation element 120 onboard the device 100 is preferably used to present the event data to the user 90.

This concludes the description of presently preferred embodiments of the invention. The foregoing description has been presented for the purpose of illustration and is not intended to be exhaustive or to limit the invention to the precise form disclosed. Other modifications, variations and alterations are possible in light of the above teaching and will be apparent to those skilled in the art, and may be used in the design and manufacture of other embodiments according to the present invention without departing from the spirit and scope of the invention. It is intended the scope of the invention be limited not by this description but only by the claims forming a part of this application and/or any patent issuing herefrom.

What is claimed is:

1. A bio-threat disease alert infrastructure system, for use with a plurality of bio-threat disease alert devices and collected quantitative data associated with a bio-threat disease, the collected quantitative data obtained from a database, the system comprising:
   (a) a receiving element operatively receiving a result of a bio-threat disease test from a biological test reader element of at least one of the plurality of devices;
   (b) an analyzing processor operatively applying one or more statistical algorithms to the collected quantitative data and the test result to precisely estimate disease event data, wherein the disease event data comprises time data and position data associated with an event in the development of a bio-threat disease;
   (c) an encoding processor to encode the disease event data into a bio-threat disease alert signal; and
   (d) a transmitting element operatively transmitting the disease alert signal to at least one of the plurality of devices;
   wherein the time data and/or the position data of the disease event is personalized to the at least one of the plurality of devices based on geographical location and personal data associated with the at least one of the plurality of devices, and the analyzing processor precisely estimates the time data and/or the position data of said at least one said disease event;
   wherein the analyzing processor precisely estimates the disease event data for said at least one said disease event which (i) occurred at a then previous time at or after a beginning of the bio-threat disease, (ii) is occurring substantially in a then present time, and/or (iii) is predicted to occur at a then future time; and
   wherein the analyzing processor applies the statistical algorithms with reference to (A) clinical parameters, (B) sociological data (C) medical infrastructure data, and (D) geophysics information.

2. A system according to claim 1, wherein the analyzing processor precisely estimates the time data of at least one said disease event which has occurred, is occurring, and/or is predicted to occur substantially geographically local and/or regional to the device.

3. A system according to claim 1, wherein the analyzing processor precisely estimates the disease event data in the form of one or more visually presentable (a) textual data, (b) graphical data, and/or (c) colored indicator light data.

4. A system according to claim 1, wherein the analyzing processor precisely estimates the disease event data in the form of visually and/or audibly presentable data.

5. A system according to claim 1, wherein the analyzing processor precisely estimates the position data of at least one said disease event in the form of (a) descriptive place name data, (b) numerical co-ordinate system data, and/or (c) graphical map and/or drawing data.

6. A system according to claim 1, wherein the analyzing processor precisely estimates the time data and/or the position data of at least one said disease event on a local, regional, national, international and/or worldwide scale.

7. A system according to claim 1, wherein the analyzing processor precisely estimates the time data and/or the position data of: (a) a progression of the bio-threat disease towards and/or through a location; (b) a rate of expansion and/or propagation of the bio-threat disease; (c) an evolution and/or mutation of one or more strains of the bio-threat disease; (d) an efficacy of one or more bio-markers in identifying the bio-threat disease; and/or (e) one or more intensities of bio-threat disease infection and/or a most infected area.

8. A system according to claim 1, wherein the analyzing processor precisely estimates the time data and/or the position data of: an efficacy of one or more treatments for the bio-threat disease, and/or a resistance of the bio-threat disease to said one or more treatments.

9. A system according to claim 1, adapted for use with one or more of the following as the device: (a) a biological test reader device; (b) a disposable, consumable and/or reusable biological test device; (c) an integrated cell phone and biological test reader device; (d) a cellular telephone; (e) a mobile communications device; (f) a personal digital assistant; (g) a desktop computer; (h) a laptop computer; (i) a navigation device; (j) a digital audio player; (k) a camera; (l) a gaming device; (m) a television; and (n) a radio.

10. A method of transmitting a bio-threat disease alert signal, for use with a bio-threat disease alert infrastructure system, a plurality of bio-threat alert devices, and collected quantitative data, the collected quantitative data obtained from at least one database and associated with a bio-threat disease, the method comprising:
 (a) a receiving step of receiving a result of a bio-threat disease test from a biological test reader element of at least one of the plurality of devices by a receiving element of the system;
 (b) a statistical analysis step of applying statistical algorithms to the collected quantitative data and the test result, using an analyzing processor of the system, to precisely estimate disease event data, wherein the disease event data comprises time data and position data associated with an event in the development of a bio-threat disease;
 (c) an encoding step of using an encoding processor of the system to encode the disease event data into a bio-threat disease alert signal; and
 (d) a transmitting step of using the system to transmit the bio-threat disease alert signal to the at least one of the plurality of devices;
 wherein the time data and/or the position data of the disease event is personalized to the at least one of the plurality of devices based on geographical location and personal data associated with the at least one of the plurality of devices, and in the statistical analysis step, the analyzing processor precisely estimates the time data and/or the position data of said at least one said disease event;
 wherein in the statistical analysis step, the analyzing processor precisely estimates the disease event data for at least one said disease event which (i) occurred at a then previous time at or after a beginning of the bio-threat disease, (ii) is occurring substantially in a then present time, and/or (iii) is predicted to occur at a then future time; and
 wherein in the statistical analysis step, the analyzing processor applies the statistical algorithms with reference to (A) clinical parameters, (B) sociological data, (C) medical infrastructure data, and (D) geophysics information.

11. A method according to claim 10, wherein in the statistical analysis step, the analyzing processor precisely estimates the time data of at least one said disease event which has occurred, is occurring, and/or is predicted to occur substantially geographically local and/or regional to the device.

12. A method according to claim 10, wherein in the statistical analysis step, the analyzing processor precisely estimates the disease event data in the form of one or more visually presentable (a) textual data, (b) graphical data, and/or (c) colored indicator light data.

13. A method according to claim 10, wherein in the statistical analysis step, the analyzing processor precisely estimates the disease event data in the form of visually and/or audibly presentable data.

14. A method according to claim 10, wherein in the statistical analysis step, the analyzing processor precisely estimates the position data of at least one said disease event in the form of (a) descriptive place name data, (b) numerical co-ordinate system data, and/or (c) graphical map and/or drawing data.

15. A method according to claim 10, wherein in the statistical analysis step, the analyzing processor precisely estimates the time data and/or the position data of at least one said disease event on a local, regional, national, international and/or worldwide scale.

16. A method according to claim 10, wherein in the statistical analysis step, the analyzing processor precisely estimates the time data and/or the position data of: (a) a progression of the bio-threat towards and/or through a location; (b) a rate of expansion and/or propagation of the bio-threat disease; (c) an evolution and/or mutation of one or more strains of the bio-threat disease; (d) an efficacy of one or more bio-markers in identifying the bio-threat disease; and/or (e) one or more intensities of bio-threat disease infection and/or a most infected area.

17. A method according to claim 10, wherein in the statistical analysis step, the analyzing processor precisely estimates the time data and/or the position data of: an efficacy of one or more treatments for the bio-threat disease, and/or a resistance of the bio-threat disease to said one or more treatments.

18. A method according to claim 10, wherein in the encoding step, the alert signal is adapted for reception by one or more of the following devices, after the transmitting step: (a) a biological test reader device; (b) a disposable, consumable and/or reusable biological test device; (c) an integrated cell phone and biological test reader device; (d) a cellular telephone; (e) a mobile communications device; (f) a personal digital assistant; (g) a desktop computer; (h) a laptop computer; (i) a navigation device; (j) a digital audio player; (k) a camera; (l) a gaming device; (m) a television; and (n) a radio.

* * * * *